United States Patent [19]

Nozawa et al.

[11] 4,315,900

[45] Feb. 16, 1982

[54] INTEGRATED PROCESS FOR THE PRODUCTION OF METHANOL AND AMMONIA

[75] Inventors: Shinkichi Nozawa, Funabashi; Kenjiro Miyashita, Chiba, both of Japan

[73] Assignee: Toyo Engineering Corporation, Tokyo, Japan

[21] Appl. No.: 193,905

[22] Filed: Oct. 6, 1980

[30] Foreign Application Priority Data

May 18, 1979 [JP] Japan .................................. 54/60272

[51] Int. Cl.³ ............................................ C01C 1/04
[52] U.S. Cl. .................................... 423/359; 518/704
[58] Field of Search ....................... 423/359, 360, 361; 518/704

[56] References Cited

U.S. PATENT DOCUMENTS

| | | | |
|---|---|---|---|
| 3,598,527 | 8/1971 | Quartulli et al. ..................... | 423/361 |
| 3,763,205 | 10/1973 | Green .................................... | 518/704 |
| 4,213,954 | 7/1980 | Pinto .................................... | 423/359 |
| 4,219,492 | 8/1980 | Konoki et al. ........................ | 518/704 |

FOREIGN PATENT DOCUMENTS 715881  9/1954  United Kingdom ............... 518/704

*Primary Examiner*—O. R. Vertiz
*Assistant Examiner*—Wayne A. Langel

[57] ABSTRACT

Disclosed is an integrated process for the production of methanol and ammonia which comprises the steps of subjecting a gaseous hydrocarbon feed to primary reforming with steam to produce a methanol synthesis gas containing $H_2$ and CO, synthesizing methanol from this methanol synthesis gas, subjecting the purge gas resulting from the methanol synthesis step to secondary reforming with steam and air to produce an ammonia synthesis gas containing $H_2$, $N_2$, CO and $CO_2$, subjecting this ammonia synthesis gas to high temperature shift conversion for the purpose of reducing its CO content, passing the CO-impoverished ammonia synthesis gas through a series of steps required for the removal of carbon oxides, and subjecting the resulting CO-free ammonia synthesis gas to ammonia synthesis.

12 Claims, 2 Drawing Figures

F I G. 2
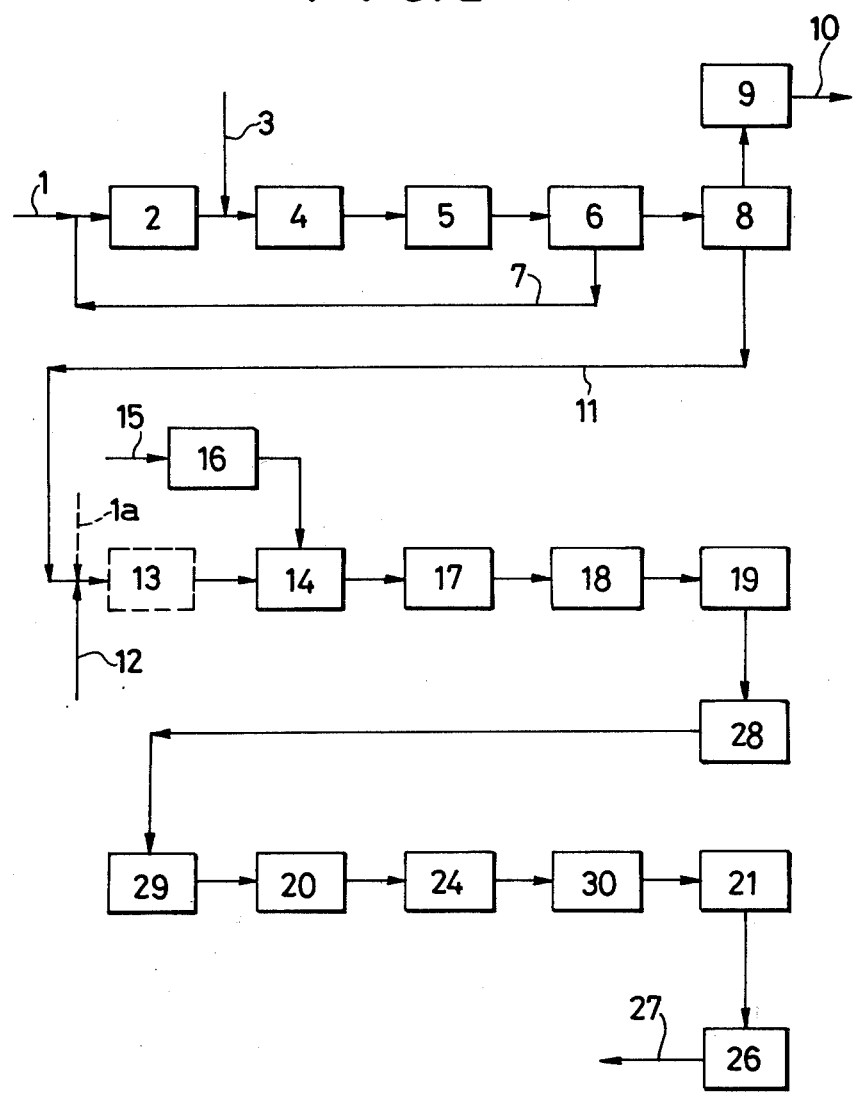

INTEGRATED PROCESS FOR THE PRODUCTION OF METHANOL AND AMMONIA

BACKGROUND OF THE INVENTION (1) Field of the Invention

This invention relates to an integrated process for the production of methanol and ammonia from a gaseous hydrocarbon feed.

(2) Description of the Prior Art

The combined production of methanol and ammonia from a hydrocarbon feed is well known as is disclosed in U.S. Pat. No. 3,598,527. According to the process of this U.S. Patent, natural gas is subjected to primary reforming with steam and to secondary reforming with steam and an oxygen-containing gas, so that a methanol synthesis gas containing hydrogen, carbon monoxide and nitrogen is produced. This methanol synthesis gas is then subjected to low pressure methanol synthesis. The effluent stream from this methanol synthesis step is separated into crude methanol and a purge gas. While the crude methanol is purified to obtain product methanol, the purge gas is subjected to high temperature and low temperature water-gas shift conversion whereby the carbon monoxide contained therein is converted into hydrogen and carbon dioxide. The gas resulting from this water-gas shift conversion step is freed of carbon oxides to a substantially complete degree by passing it through carbon dioxide removal and methanation steps, compressed to a desired ammonia synthesis pressure, and then subjected to ammonia synthesis.

When compared with the separate production of methanol and ammonia, the above-described process has several advantages such as lowered capital investment and reduced operating costs. However, it still remains to be improved in some respects. More specifically, since a methanol synthesis gas is produced by both primary reforming and secondary reforming, it contains nitrogen which is unnecessary for methanol synthesis. This lowers the effective pressure for methanol synthesis. Moreover, it is required to increase the capacities of the methanol synthesis tube, methanol synthesis gas compressor and circulating gas pump in proportion to the nitrogen content. Furthermore, during methanol synthesis, the nitrogen present in the methanol synthesis gas tends to form methylamines as impurities, thus leading to a complicated procedure for the purification of crude methanol.

SUMMARY OF THE INVENTION

It is an object of the present invention to provide an improved integrated process for the production of methanol and ammonia.

It is another object of the present invention to provide an integrated process for the production of methanol and ammonia in which the methanol to ammonia production ratio can be varied widely.

It is still another object of the present invention to provide an integrated process for the production of methanol and ammonia which involves no risk of forming methylamines as impurities.

Other objects and advantages of the present invention will become apparent from the following detailed description.

According to the present invention, there is provided an integrated process for the production of methanol and ammonia which comprises the steps of (a) subjecting a gaseous hydrocarbon feed to primary reforming with steam in the presence of a hydrocarbon reforming catalyst to produce a methanol synthesis gas containing hydrogen and carbon monoxide;

(b) subjecting the methanol synthesis gas to methanol synthesis and then separating from the resulting methanol a purge gas containing hydrogen, carbon monoxide, carbon dioxide and methane;

(c) subjecting the purge gas to secondary reforming with steam and a oxygen-containing gas to produce an ammonia synthesis gas containing hydrogen, carbon monoxide, carbon dioxide and nitrogen;

(d) subjecting the ammonia synthesis gas to high temperature shift conversion and thereby converting the carbon monoxide into hydrogen and carbon dioxide;

(e) passing the carbon monoxide-impoverished ammonia synthesis gas through a series of steps required for the removal of carbon oxides; and (f) subjecting the resulting carbon monoxide-free ammonia synthesis gas to ammonia synthesis.

BRIEF DESCRIPTION OF THE DRAWINGS

FIG. 2 is a schematic flowsheet illustrating another embodiment of the present invention.

DETAILED DESCRIPTION OF THE INVENTION

Figure 1:
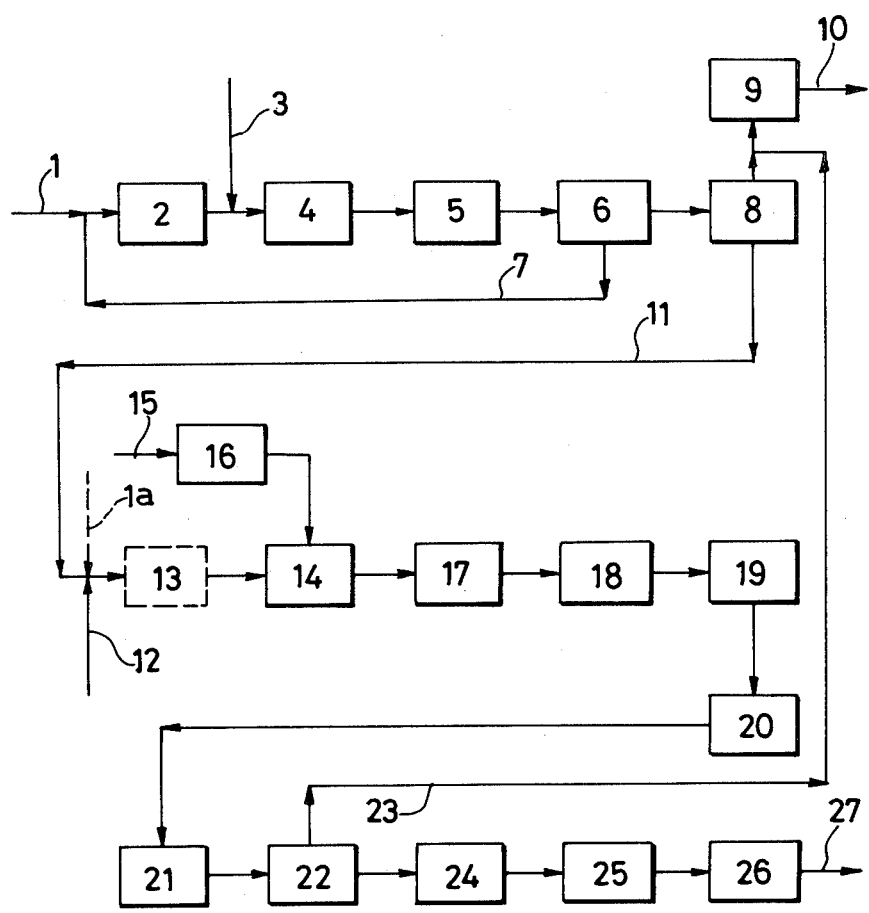
FIG. 1 is a schematic flowsheet illustrating one embodiment of the present invention.

The gaseous hydrocarbon feed used in the process of the present invention can be a member selected from the group consisting of hydrocarbons containing 1 to 4 carbon atoms and mixtures thereof. A typical example of the gaseous hydrocarbon feed is natural gas composed mainly of methane.

The primary reforming of the gaseous hydrocarbon feed is generally carried out under such conditions that the effluent stream leaving the reforming zone has a pressure of 15 to 40 $kg/cm^2$ gauge and a temperature of 800° to 900° C. In view of the decomposition rates of hydrocarbons and the selection of equipment materials, however, it is particularly preferable to carry out the primary reforming under such conditions that the effluent stream leaving the reforming zone has a pressure of 17 to 20 $kg/cm^2$ gauge and a temperature of 850° to 900° C.

The methanol synthesis process used in the present invention may preferably be a low pressure methanol synthesis process employing a pressure of 40 to 100 $kg/cm^2$ gauge, in view of the pressure at which the purge gas resulting from the methanol synthesis process is subjected to secondary reforming.

The purge gas resulting from the methanol synthesis process is then subjected to secondary reforming with steam and an oxygen-containing gas (for example, air). This secondary reforming is carried out at an outlet pressure of 39 to 49 $kg/cm^2$ and at an outlet temperature of 1,000° to 1,050° C. Where the purge gas has a high methane content, it may be subjected to additional primary reforming with steam and then to secondary reforming. Moreover, where both primary reforming and secondary reforming are employed, an additional hydrocarbon feed may be added to the purge gas according to the required ammonia production rate. Usually, air is used as the oxygen-containing gas. However, a mixture of oxygen and air in any desired proportion may be used if it is necessary for the purpose of achieving a hydrogen to nitrogen ratio of 3:1 in the gas resulting from the secondary reforming step.

The gas resulting from the secondary reforming step is then subjected to high temperature shift conversion whereby the carbon monoxide contained therein is converted into hydrogen and carbon dioxide. Thereafter, the gas is passed through a procedure for the removal of carbon oxides, so that the small amounts of carbon monoxide and carbon dioxide contained therein are removed from the remainder of the gas.

For the removal of carbon oxides, either of the following two procedures comprising a series of steps may be employed. According to one of them, the gas resulting from the high temperature shift conversion step is passed through waste heat recovery equipment, subjected to a carbon dioxide removal step, compressed (for example, to a pressure of 100 to 300 kg/cm$^2$ gauge and preferably a pressure equal to the ammonia synthesis pressure) by means of a compressor, and then subjected to methanol synthesis in the presence of a methanol synthesis catalyst to convert almost all of the carbon monoxide and carbon dioxide into methanol. Thereafter, the gas resulting from this methanol synthesis step, which contains hydrogen, nitrogen, methane, argon, and very small amount of carbon monoxide and carbon dioxide, is subjected to conventional methanation whereby the residual carbon monoxide and carbon dioxide are converted into methane.

Another procedure is the one which is commonly employed in the production of an ammonia synthesis gas. More specifically, the gas resulting from the high temperature shift conversion step is freed of carbon oxides by passing it through a series of steps including low temperature shift conversion, carbon dioxide removal and methanation. This procedure is more fully described, for example, in U.S. Pat. No. 3,598,527.

After being passed through the above-described procedure for the removal of carbon oxides, the gas is subjected to ammonia synthesis, for example, at a pressure of 100 to 300 kg/cm$^2$ gauge and a temperature of 380° to 500° C.

The present invention will now be described in more detail with reference to FIGS. 1 and 2.

Referring first to FIG. 1, there is illustrated an embodiment of the invention in which the procedure for the removal of carbon oxides comprises carbon dioxide removal, methanol synthesis and methanation. In the embodiment of FIG. 1, a hydrocarbon feed or natural gas under pressure is introduced through a pipeline 1, combined with a hydrogenation gas fed through a pipeline 7, and then preheated to a temperature of the order of 400° C. Thereafter, in order to hydrogenate sulfur compounds which are poisonous to the catalysts used for reforming with steam, methanol synthesis and ammonia synthesis and then remove the resulting products by adsorption, the natural gas is passed through desulfurization equipment 2 containing Co-Mo catalyst, zinc oxide and the like.

Steam is fed through a pipeline 3 and added to the desulfurized natural gas in an amount of 2 to 4 moles per atomic weight of the carbon contained therein. The resulting natural gas-steam mixture is heated to a temperature of the order of 600° C. and then introduced into a primary reformer 4 where, under the influence of a nickel catalyst, most of the natural gas is decomposed into hydrogen, carbon monoxide and carbon dioxide. This primary reforming is carried out under such conditions that the effluent stream leaving the primary reformer 4 has a pressure of 15 to 40 kg/cm$^2$ gauge and a temperature of 800° to 900° C.

After leaving the primary reformer 4, the hot reformed gas flows into waste heat recovery equipment 5 where the waste heat recovered therefrom is utilized for the generation of steam, for the preheating of boiler feedwater, as a heat source for the distillation of crude methanol, and for other purposes. Thereafter, the hot reformed gas is cooled to ordinary temperature and the resulting condensate is separated therefrom. The cooled reformed gas, which now constitutes a methanol synthesis gas, enters a compressor 6 where it is compressed to a pressure of 40 to 100 kg/cm$^2$ gauge.

A portion of the methanol synthesis gas leaving the compressor 6 is returned through the pipeline 7 to the desulfurization equipment 2 and used as a hydrogenation gas.

The remainder of the methanol synthesis gas is introduced into methanol synthesis equipment 8, combined with the gas circulating within this equipment, compressed by means of a circulator, and preheated. Then, this methanol synthesis gas flows into a methanol synthesis converter containing a conventional copper catalyst (for example, a Cu-Zn or Cu-Zn-Cr catalyst), where methanol is synthesized at a temperature of 240° to 270° C.

The effluent gas stream from the methanol synthesis converter is cooled to effect condensation of crude methanol. The condensed and separated crude methanol is introduced into methanol distillation equipment 9 were high-boiling and low-boiling impurities are removed therefrom. Thus, refined methanol is withdrawn through a pipeline 10.

On the other hand, a portion of the gas stream from which crude methanol has been removed is discharged as a purge gas through a pipeline 11 in order to avoid accumulation of methane, nitrogen and other materials which do not take part in methanol synthesis. The remainder of the gas stream, which constitutes a circulating gas, is combined with methanol synthesis gas and reused for methanol synthesis. It is to be understood that, in some cases, the methanol synthesis equipment involves no gas circulation and all of the gas stream from which crude methanol has been separated is fed as a purge gas to the next step.

The aforesaid purge gas preferably comprises 70 to 80 mole % of hydrogen, 10 to 20 mole % of methane, 1 to 2 mole % of carbon monoxide, 1 to 2 mole % of carbon dioxide, 0 to 1 mole % of methanol, and 0 to 5 mole % of nitrogen.

The purge gas fed through the pipeline 11 is subsequently used as the raw material for ammonia synthesis. After this purge gas is preheated to a temperature of the order of 300° C., steam fed through a pipeline 12 is added thereto in an amount of 3 to 4 moles per atomic weight of the carbon contained therein. The resulting purge gas-steam mixture is further heated to a temperature of 500° C. and introduced into a primary reformer 13.

Within the primary reformer 13, the methane and methanol present in the purge gas are decomposed with steam in the presence of a nickel catalyst and a portion thereof is converted into hydrogen, carbon monoxide and carbon dioxide. This primary reforming is carried out under such conditions that the process stream leaving the primary reformer 13 has a pressure of 40 to 50 kg/cm$^2$ gauge and a temperature of 830° to 900° C.

After leaving the primary reformer 13, the hot process stream is immediately introduced into a secondary reformer 14. On the other hand, air is compressed to a pressure of 40 to 50 kg/cm² gauge by means of an air compressor 16, heated to a temperature of 650° to 850° C., and then fed through a pipeline 15 to the secondary reformer 14.

Within the secondary reformer 14, the methane, hydrogen and carbon monoxide present in the hot process stream are partially burned with the oxygen contained in the air. Also within the secondary reformer 14, most of the methane is reacted with steam and thereby decomposed into hydrogen, carbon monoxide and carbon dioxide. The Hot process stream leaving the secondary reformer 14 has a pressure of 39 to 49 kg/cm² gauge and a temperature of 1,000° to 1,050° C.

Depending on the methane content of the purge gas resulting from the methanol synthesis step, the primary reformer 13 may be omitted. Alternatively, if it is desired to increase the ammonia production rate, a make-up natural gas feed may be added through a pipeline 1a to the purge gas introduced into the primary reformer 13.

The hot process stream leaving the secondary reformer 14 is then introduced into waste heat recovery equipment 17 where waste heat is recovered in the form of high pressure steam. The process stream leaving the waste heat recovery equipment 17 is maintained at a temperature of 350° to 370° C. and subsequently fed to a high temperature shift converter 18 containing an iron-chromium catalyst. Under the influence of this catalyst, the carbon monoxide present in the process stream emerging from the secondary reformer 14 is converted into hydrogen and carbon dioxide, so that the process stream leaving the high temperature shift converter 18 has a carbon monoxide content of approximately 2.0 to 2.5 mole % (on a dry gas basis).

The process stream leaving the high temperature shift converter 18, which is a hot gaseous mixture having a temperature of 400° to 420° C., then enters waste heat recovery equipment 19 where the waste heat recovered therefrom is utilized for the generation of high pressure steam, the preheating of boiler feedwater, the preheating of the gas stream fed to a methanator, and for other purposes. Furthermore, the waste heat is also utilized as a heat source for the separation of product ammonia in an absorption refrigerator.

After being cooled in the waste heat recovery equipment 19, the process stream flows into carbon dioxide removal equipment 20 where the carbon dioxide present in the process stream is removed by passing the process stream through monoethanolamine, an aqueous solution of potassium carbonate, or other absorbing fluids. Thus, the carbon dioxide content of the process stream is reduced to 1 to 2 mole % (on a dry gas basis).

The process stream leaving the carbon dioxide removal equipment 20 is subsequently compressed to a pressure of approximately 100 to 300 kg/cm² gauge by means of a compressor 21. Then, the compressed process stream enters methanol synthesis equipment 22 where it is preheated and passed through a methanol synthesis converter containing a methanol synthesis catalyst (for example, the aforesaid copper catalyst). Under the influence of this catalyst and at a temperature of 210° to 270° C., the carbon monoxide and carbon dioxide present in the process stream are reacted with hydrogen to produce methanol. Thus, the process stream leaving the methanol synthesis converter has a carbon monoxide content of as low as 0.1 to 0.5 mole % and a carbon dioxide content of as low as 0.3 to 0.5 mole % (on a dry gas basis).

In some cases, this methanol synthesis step may be carried out by withdrawing the process stream from an intermediate stage of the aforesaid compressor 21 and passing it through the methanol synthesis equipment 22.

The methanol present in the effluent stream from the methanol synthesis converter is condensed by cooling and separated from the process stream. The resulting crude methanol is fed through a pipeline 23 to the methanol distillation equipment 9, thus constituting a portion of the refined product methanol.

The process stream leaving the methanol synthesis equipment 22 is preheated to a temperature of the order of 300° C. and then fed to a methanator 24 where, under the influence of a nickel catalyst, the very small amounts of carbon monoxide and carbon dioxide present in the process stream are reacted with hydrogen and thereby converted into methane.

The hot process stream leaving the methanator 24 flows into waste heat recovery equipment 25 where the waste heat recovered therefrom is utilized for the preheating of boiler feedwater. The process stream is further water-cooled to ordinary temperature. The process stream leaving the waste heat recovery equipment 25 flows into ammonia synthesis equipment 26 where it is combined with the stream discharged from the circulator and then cooled by contact with ammonia used as a coolant. Thus, the ammonia present in the stream circulating within the ammonia synthesis equipment 26 is condensed and separated by means of a first separator provided therewithin. Thereafter, the circulating stream is preheated and introduced into an ammonia synthesis converter where, under the influence of an iron catalyst, ammonia is synthesized at a temperature of 380° to 500° C. and a pressure of 100 to 300 kg/cm² gauge.

The hot gas stream leaving the ammonia synthesis tube is passed through a boiler or a boiler feedwater preheater to recover waste heat therefrom, and finally water-cooled to ordinary temperature. The ammonia present in the hot gas stream is condensed during this cooling, separated by means of a second separator provided within the ammonia synthesis equipment 26, and withdrawn through a pipeline 27 to obtain product ammonia.

Referring now to FIG. 2, there is illustrated another embodiment of the invention in which the procedure for the removal of carbon oxides comprises low temperature shift conversion, carbon dioxide removal and methanation. In the embodiment of FIG. 2, the steps ranging from the desulfurization of a gaseous hydrocarbon feed or natural gas to the waste heat recovery of the gas resulting from the high temperature shift conversion step are the same as those described in connection with the embodiment of FIG. 1. Accordingly, no detailed description of these steps is given here.

The process stream leaving the waste heat recovery equipment 19 is introduced into a low temperature shift converter 28 where most of the residual carbon monoxide is converted into hydrogen and carbon dioxide by contacting the process stream with a conventional copper catalyst at a temperature of 200° to 270° C.

The process stream leaving the low temperature shift converter 28 is introduced into waste heat recovery equipment 29 where the waste heat recovered therefrom is utilized for the regeneration of carbon dioxide removal equipment 20, the preheating of boiler feedwater, and the like.

After being cooled in the waste heat recovery equipment 29, the process stream is then introduced into carbon dioxide removal equipment 20 where carbon dioxide is removed in the same manner as described previously.

After the removal of carbon dioxide, the process stream is preheated to a temperature of the order of 300° C. and introduced into a methanator 24 where the carbon oxides present therein are converted into methane by reacting them with hydrogen under the influence of a nickel catalyst suitable for methanation.

The process stream leaving the methanator 24 enters waste heat recovery equipment 30 where the waste heat recovered therefrom is utilized for the preheating of boiler feedwater, and the like. Thereafter, the process stream is water-cooled to ordinary temperature.

The process stream leaving the waste heat recovery equipment 30 is compressed to a desired ammonia synthesis pressure by means of a compressor 21 and then subjected to ammonia synthesis in the same manner as described previously.

The above-described integrated process for the production of methanol and ammonia has several advantages as outlined below.

(1) Since no nitrogen is admitted into the methanol synthesis process, the increased capacities of the compressors, methanol synthesis converter and the like due to the presence of nitrogen can be avoided.

(2) Since an ammonia synthesis gas is obtained by reforming the purge gas derived from the methanol synthesis process, the methanol to ammonia production ratio can be controlled at will, especially by introducing an additional hydrocarbon feed into the reforming step.

(3) Since separate reformers are used for the production of a methanol synthesis gas and an ammonia synthesis gas, the reforming can be carried out under pressure and temperature conditions suitable for the respective gases.

(4) Where methanol synthesis is employed for the removal of carbon monoxide and carbon dioxide in the ammonia synthesis process, the production rate of ammonia is reduced. As a result, the feed rate of air used for secondary reforming and hence the power consumption of the air compressor and the like is decreased. Moreover, the decreased feed rate of air used for secondary reforming causes a drop in flame temperature and, therefore, the selection of a proper catalyst is facilitated from the viewpoint of thermal resistance.

(5) Where methanol synthesis is employed for the removal of carbon monoxide and carbon dioxide in the ammonia synthesis process, the amount of carbon dioxide leaking from the carbon dioxide removal step may be 2 to 3 mole % rather than 0.01 to 0.1 mole % as has been required in the prior art. Thus, the carbon dioxide removal step can be designed and operated with greater ease.

(6) Where methanol synthesis is employed for the removal of carbon monoxide and carbon dioxide in the ammonia synthesis process, the low temperature shift conversion step which requires much care in respect of catalyst and operation can be omitted. Thus results in enhanced operability.

(7) Where methanol synthesis is employed for the removal of carbon monoxide and carbon dioxide in the ammonia synthesis process, methanation is carried out at high pressure, so that this reaction proceeds beneficially from the viewpoint of chemical equilibrium. Thus, a smaller amount of catalyst may used as compared with the prior art process employing a pressure of the order of 25 kg/cm$^2$ gauge.

The present invention is further illustrated by the following example.

EXAMPLE

According to the embodiment of the invention illustrated in FIG. 1, methanol and ammonia were produced with the material balance given below.

In this example, the consumption of natural gas used as the gaseous hydrocarbon feed amounted to $11.6 \times 10^8$ Nm$^3$/year (LHV; 8,652 kcal/Nm$^3$). This represents a reduction of 8% as compared with the total consumption of natural gas (i.e., $12.5 \times 10^8$ Nm$^3$/year) required in the conventional separate production of equal amounts of methanol and ammonia. In addition, the present invention provided the omission of the compressor for natural gas fed to the ammonia production process, the usability of utilities in common, a decrease in plot area, and other beneficial effects as described previously.

MATERIAL BALANCE (1) Methanol Synthesis Process

| vol. % | Natural gas feed | Hydrogenated and desulfurized gas | Process steam | Gas entering methanol synthesis equipment | Crude methanol | Purge gas |
|---|---|---|---|---|---|---|
| CH$_4$ | 88.00 | 5.12 | — | 5.12 | — | 17.43 |
| C$_2$H$_6$ | 4.80 | — | — | — | — | — |
| C$_3$H$_8$ | 1.46 | — | — | — | — | — |
| C$_4$H$_{10}$ | 0.26 | — | — | — | — | — |
| CO$_2$ | 0.55 | 7.37 | — | 7.37 | — | 1.57 |
| N$_2$ | 4.93 | 1.30 | — | 1.30 | — | 4.53 |
| H$_2$ | — | 71.32 | — | 71.32 | — | 75.13 |
| CO | — | 14.89 | — | 14.89 | — | 1.02 |
| CH$_3$OH | — | — | — | — | 100.0 | 0.32 |
| Dry gas (Nm$^3$/hr) | 91,693 | 6,916 | — | 353,852 | 73,980 | 98,759 |
| H$_2$O (Nm$^3$/hr) | — | 35 | 251,846 | 311 | 24,006 | 28 |

(2) Ammonia Synthesis Process

| | Purge gas from methanol synthesis process | Process steam | Gas leaving primary reformer | Process air | Gas leaving secondary reformer | Gas leaving high temperature shift converter | Gas leaving CO2 removal equipment | Gas leaving methanol synthesis equipment | By-product methanol | Gas leaving methanator | Product ammonia | Purge gas |
|---|---|---|---|---|---|---|---|---|---|---|---|---|
| CH4 | 17.43 | — | 9.38 | — | 0.82 | 0.77 | 0.83 | 0.97 | — | 1.14 | — | 15.76 |
| H2 | 75.13 | — | 79.42 | — | 66.94 | 68.80 | 73.58 | 74.09 | — | 73.94 | — | 58.70 |
| N2 | 4.53 | — | 3.75 | — | 20.62 | 19.46 | 20.81 | 24.50 | — | 24.65 | — | 19.54 |
| CO | 1.02 | — | 4.86 | — | 8.50 | 2.39 | 0.23 | 0.09 | — | — | — | — |
| CO2 | 1.57 | — | 2.59 | — | 2.89 | 8.36 | 2.00 | 0.08 | — | — | — | — |
| CH3OH | 0.32 | — | — | — | — | — | — | — | 100.0 | — | — | — |
| Ar | — | — | — | — | 0.23 | 0.22 | 0.23 | 0.27 | — | 0.27 | — | 3.83 |
| NH3 | — | — | — | — | — | — | — | — | — | — | 100.0 | 2.17 |
| Dry gas (Nm³/hr) | 98,759 | — | 119,335 | 37,736 | 164,453 | 174,264 | 162,951 | 137,819 | 7,140 | 137,005 | 63,524 | 9,610 |
| H2O (Nm³/hr) | 28 | 69,297 | 58,746 | — | 65,797 | 55,986 | 372 | 19 | 3,208 | 361 | — | — |

What is claimed is:

1. An integrated process for the production of methanol and ammonia which comprises the steps of
    (a) subjecting a gaseous hydrocarbon feed to primary reforming with steam in the presence of a hydrocarbon reforming catalyst to produce a methanol synthesis gas containing hydrogen and carbon monoxide;
    (b) subjecting the methanol synthesis gas to methanol synthesis and then separating from the resulting methanol a purge gas containing hydrogen, carbon monoxide, carbon dioxide and methane;
    (c) subjecting the purge gas to secondary reforming with steam and an oxygen-containing gas to produce an ammonia synthesis gas containing hydrogen, carbon monoxide, carbon dioxide and nitrogen;
    (d) subjecting the ammonia synthesis gas to high temperature shift conversion and thereby converting carbon monoxide into hydrogen and carbon dioxide;
    (e) passing the carbon monoxide-impoverished ammonia synthesis gas through a series of steps required for the removal of carbon oxides; and
    (f) subjecting the resulting carbon monoxide-free ammonia synthesis gas to ammonia synthesis.

2. An integrated process as claimed in claim 1 wherein, prior to the secondary reforming, the purge gas is subjected to additional primary reforming with steam.

3. An integrated process as claimed in claim 2 wherein a make-up hydrocarbon feed is added to the purge gas.

4. An integrated process as claimed in claim 1 wherein the series of steps required for the removal of carbon oxides comprises carbon dioxide removal, methanol synthesis and methanation.

5. An integrated process as claimed in claim 4 wherein the methanol synthesis is carried out at a pressure of 100 to 300 kg/cm² gauge and a temperature of 210° to 270° C.

6. An integrated process as claimed in claim 1 wherein the gaseous hydrocarbon feed comprises one or more hydrocarbons containing 1 to 4 carbon atoms.

7. An integrated process as claimed in claim 1 wherein the primary reforming is carried out at a pressure of 15 to 40 kg/cm² gauge and a temperature of 800° to 900° C.

8. An integrated process as claimed in claim 1 wherein the methanol synthesis is carried out at a pressure of 40 to 100 kg/cm² gauge and a temperature of 240° to 270° C.

9. An integrated process as claimed in claim 1 wherein the purge gas contains 70 to 80 mole % of hydrogen, 10 to 20 mole % of methane, 1 to 2 mole % of carbon monoxide, and 1 to 2 mole % of carbon dioxide.

10. An integrated process as claimed in claim 1 wherein the oxygen-containing gas is air.

11. An integrated process as claimed in claim 1 wherein the series of steps required for the removal of carbon dioxides comprises low temperature shift conversion, carbon dioxide removal and methanation.

12. An integrated process as claimed in claim 1 wherein the ammonia synthesis is carried out at a pressure of 100 to 300 kg/cm² gauge and a temperature of 380° to 500° C.

* * * * *